(12) United States Patent
Jones

(10) Patent No.: US 10,380,751 B1
(45) Date of Patent: Aug. 13, 2019

(54) ROBOT VISION IN AUTONOMOUS UNDERWATER VEHICLES USING THE COLOR SHIFT IN UNDERWATER IMAGING

(71) Applicant: The United States of America, as represented by the Secretary of the Navy, Washington, DC (US)

(72) Inventor: Jacob A. Jones, Chesapeake, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/910,145

(22) Filed: Mar. 2, 2018

Related U.S. Application Data

(60) Provisional application No. 62/597,777, filed on Dec. 12, 2017.

(51) Int. Cl.
*G06T 7/00* (2017.01)
*G06T 7/55* (2017.01)
(Continued)

(52) U.S. Cl.
CPC ................... *G06T 7/55* (2017.01); *G01J 3/50* (2013.01); *G01K 13/02* (2013.01); *G01N 33/18* (2013.01);
(Continued)

(58) Field of Classification Search
CPC ... G06T 7/55; G06T 7/90; G06T 2207/10024; G06T 2207/10028; G06T 2207/30252;
(Continued)

(56) References Cited

U.S. PATENT DOCUMENTS

| 7,417,666 B2 | 8/2008 | Kaltenbacher et al. |
| 7,796,809 B1 | 9/2010 | Carder et al. |

(Continued)

OTHER PUBLICATIONS

The United States Navy, "The Navy unmanned undersea vehicle (UUV) master plan," (2004), available at www.navy.mil/navydata/technology/uuvmp.pdf, last accessed Jan. 26, 2018.

(Continued)

*Primary Examiner* — Zhihan Zhou
(74) *Attorney, Agent, or Firm* — Naval Postgraduate School; Scott Bell

(57) ABSTRACT

A robot vision system for generating a 3D point cloud of a surrounding environment through comparison of unfiltered and filtered images of the surrounding environment. A filtered image is captured using a camera filter which tends to pass certain wavelength bandwidths while mitigating the passage of other bandwidths. A processor receives the unfiltered and filtered images, pixel matches the unfiltered and filtered images, and determines an image distance for each pixel based on comparing the color coordinates determined for that pixel in the unfiltered and filtered image. The image distances determined provides a relative distance from the digital camera to an object or object portion captured by each pixel, and the relative magnitude of all image distances determined for all pixels in the unfiltered and filtered images allows generation of a 3D point cloud representing the object captured in the unfiltered and filtered images.

20 Claims, 6 Drawing Sheets

(51) Int. Cl.
*G06T 7/90* (2017.01)
*H04N 9/097* (2006.01)
*G01K 13/02* (2006.01)
*G01J 3/50* (2006.01)
*G01N 33/18* (2006.01)

(52) U.S. Cl.
CPC ............... *G06T 7/90* (2017.01); *H04N 9/097* (2013.01); *G01K 2013/026* (2013.01); *G06T 2207/10024* (2013.01); *G06T 2207/10028* (2013.01); *G06T 2207/30252* (2013.01)

(58) Field of Classification Search
CPC ..... G01J 3/50; G01K 13/02; G01K 2013/026; G01N 33/18; H04N 9/097
See application file for complete search history.

(56) References Cited

U.S. PATENT DOCUMENTS

| | | | | |
|---|---|---|---|---|
| 8,502,974 | B2* | 8/2013 | Johnsen | G01J 3/06 348/148 |
| 8,767,295 | B2 | 7/2014 | Johnson | |
| 9,812,018 | B2 | 11/2017 | Celikkol et al. | |
| 2016/0042513 | A1* | 2/2016 | Yudovsky | G06F 19/321 382/128 |
| 2017/0003121 | A1* | 1/2017 | Brandli | G01B 11/25 |
| 2017/0079530 | A1* | 3/2017 | DiMaio | A61B 5/0075 |
| 2018/0299556 | A1* | 10/2018 | Marcus | G01S 17/89 |

OTHER PUBLICATIONS

Button et al., "A Survey of Missions for Unmanned Undersea Vehicles," RAND Corporation (2009), available at https://www.rand.org/content/dam/rand/pubs/monographs/2009/RAND_MG808.pdf, ;ast accessed Jan. 26, 2018.
Hill, "Robot vision vs computer vision, what's the difference?" (2016), available at http://blog.robotiq.com/robot-vision-vs-computer-visionwhats-the-difference, last accessed Jan. 26, 2018.
Cain et al., "Laser based rangefinder for underwater applications," Proceedings of the American Control Conference, (2012).
Hanson et al., "Short-range sensor for underwater robot navigation using line-lasers and vision," 10th IFAC Conference on Maneuvering Control of Marine Craft (2015).2015.
Karras et al., "Localization of an underwater vehicle using an IMU and a laser-based vision system," IEEE Proceedings 15th Mediterranean Conference on Control & Automation (2007).
Jaffe, "Development of a laser line scan LiDAR imaging system for AUV use," Scripps Institution of Oceanography, Final Report (2010).
Campos et al., "Evaluation of a laser based structured light system for 3D reconstruction of underwater environments," 5th MARTECH International Workshop on Marine Technology (2013).
Payeur et al., "Dense stereo range sensing with marching pseudo-random patterns," Fourth Canadian Conference on Computer and Robot Vision (2007).
Fernandez et al., "Absolute phase mapping for one-shot dense pattern projection," IEEE Computer Society Conference on Computer Vision and Pattern Recognition Workshops (2010).
Sarafraz et al., A structured light method for underwater surface reconstruction. ISPRS J. Photogramm. Remote Sens 114 (2016).
Ishii et al., "High-speed 3D image acquisition using coded structured light projection," IEEE RSJ International Conference on Intelligent Robotics and Systems (2007).
Huang et al., "Fast three-step phase-shifting algorithm," Appl. Opt. 45 (2006).
Bruno et al., "Experimentation of structured light and stereo vision for underwater 3D reconstruction," ISPRS J. Photogramm. Remote Sens, 66(4) (2011).
Campbell et al., "A robust visual odometry and precipice detection system using consumer-grade monocular vision," IEEE International Conference on Robotics and Automation (2005).
Irani et al., "Recovery of ego-motion using image stabilization," 1994 IEEE Computer Society Conference on Computer Vision and Pattern Recognition (1994).
Burger et al., "Estimating 3-D egomotion from perspective image sequences," IEEE Trans. Pattern Anal. Mach. Intell 12(11) (1990).
Jaegle et al., "Fast, robust, continuous monocular egomotion computation," IEEE International Conference on Robotics and Automation (2016).
Botelho et al., "Visual odometry and mapping for underwater autonomous vehicles," 6th Latin American Robotics Symposium (2009).
Shakernia et al., "Omnidirectional egomotion estimation from back-projection flow," IEEE Conference on Computer Vision and Pattern Recognition (2003).
Garcia et al., "On the way to solve lighting problems in underwater imaging," IEEE Proceedings Oceans 2002 (2002).
Vasilescu et al.,"Color-accurate underwater imaging using perceptual adaptive illumination," Autonomous Robots (2011).
Pope et al., "Absorption spectrum (380-700nm) of pure water. Integrating cavity measurements," Appl. Opt 36(33) (1997).
Jones, "The historical background and evolution of the colorimetry report," J. Opt. Soc. Am 33(10) (1943).
Smith et al., "The C.I.E. colorimetric standards and their use," Trans. Opt. Soc. 33(3) (1931).
Morrow et al., "A submersible radiometer for measuring solar UV irradiance over a wide dynamic range," Proc. SPIE Ultraviolet ground- and space-based Measurements, Models, and Effects II (2003).
Pegau et al., "Absorption and attenuation of visible and near-infrared light in water: dependence on temperature and salinity," Appl. Opt, 36(24) (1997).
Rottgers et al., "Temperature and salinity correction coefficients for light absorption by water in the visible to infrared spectral region," Opt. Express, 22(21) (2014).
Lee et al., "Hyperspectral remote sensing for shallow water," Appl. Opt, 38(18) (1999).
Mobley et al., "Effects of optically shallow bottoms on upwelling radiances: bidirectional reflectance distribution function effects," Limnol. Oceanogr, 48(1) (2003).
English et al., "Determining bottom reflectance and water optical properties using unmanned underwater vehicles under clear or cloudy skies," J. Atmospheric Ocean. Technol. (2006).
Cronin et al., "The linearly polarized light field in clear, tropical marine waters: spatial and temporal variation of light intensity, degree of polarization and e-vector angle," J. Exp. Biol, 204 (2001). Available: https://jeb.biologists.org/content/204/14/2461.
Xie et al., "A Novel Sub-Pixel Matching Algorithm Based on Phase Correlation Using Peak Calculation," The International Archives of the Photogrammetry, Remote Sensing and Spatial Information Sciences, vol. XLI-B1 (2016).
Hamzah et al., "A Pixel to Pixel Correspondence and Region of Interest in Stereo Vision Application," 2012 IEEE Symposium on Computers and Infomatics (2012).
Takita et al., "A Sub-pixel Correspondence Search Technique for Computer Vision Applications," IEICE Trans. Fundamentals (E87) (2004).
Birchfield et al., "Depth Discontinuities by Pixel-to-Pixel Stereo," Proceedings of the 1998 IEEE International Conference on Computer Vision (1998).
Uchida et al., "Fast and Accurate Template Matching using Pixel Rearrangement on the GPU," 2011 Second International Conference on Networking and Computing (2011).
Yaguchi et al., "Optimal Pixel Matching between Images," In: Wada T., Huang F., Lin S. (eds) Advances in Image and Video Technology (2009).
Yaguchi et al., "Full Pixel Matching between Images for Non-linear Registration of Objects," Information and Media Technologies 5(2) (2010).

(56) References Cited

OTHER PUBLICATIONS

Chen et al., "Pixel-Based Correspondence and Shape Reconstruction for Moving Objects," 2009 IEEE 12th International Conference on Computer Vision Workshops (2009).

* cited by examiner

ROBOT VISION IN AUTONOMOUS UNDERWATER VEHICLES USING THE COLOR SHIFT IN UNDERWATER IMAGING

RELATION TO OTHER APPLICATIONS

This patent application is a nonprovisional of and claims benefit from U.S. Provisional application 62/597,777 filed Dec. 12, 2017, which is hereby incorporated by reference in its entirety.

FIELD OF THE INVENTION

One or more embodiments relates generally to an apparatus and method for a robot vision system to generate a 3D point cloud of a surrounding environment through analysis of color shifts in captured images of the surrounding environment.

BACKGROUND

Robot vision is the combination of hardware and software algorithms to allow a robot to process its environment by gathering and processing various signals originating or interacting with the environment. Several such systems are based on the collection and analysis of light, such as laser rangefinders, structured light systems, visual odometry systems, and others. There are currently many sensors and techniques under development for underwater robot vision.

Laser-based sensors project a laser and calculate ranges based on time-of-flight calculations while making some assumptions about the scene geometry. See e.g. Cain et al., "Laser based rangefinder for underwater applications," Proceedings of the American Control Conference, (2012). A particular method utilizes two line lasers and a camera to provide a two dimensional and three-dimensional representation of the environment. See e.g. Cain et al., "Laser based rangefinder for underwater applications," *Proceedings of the American Control Conference*, (2012); see also Hanson et al., "Short-range sensor for underwater robot navigation using line-lasers and vision," IFAC-PapersOnLine 48-16 (2015). Other approaches have also been developed. See Karras et al., "Localization of an underwater vehicle using an IMU and a laser-based vision system," *IEEE Proceedings 15th Mediterranean Conference on Control & Automation* (2007); see also Jaffe, "Development of a laser line scan LiDAR imaging system for AUV use," Scripps Institution of Oceanography, La Jolla, Calif., Final Report (2010).

Structured light is another technique receiving attention. Structured light works like laser scanners by projecting light and viewing the reflected light with a camera set at an angle. The difference is largely that light projected has a specific pattern rather than simply a point or beam. Comparing the expected pattern (assuming no object in the path of the light) to the actual return can determine the shape of the object that caused the distortion. The projected light may be black and white, colored or even at higher frequencies such as infrared or ultraviolet and may be projected in an infinite variety of patterns. See e.g. Campos et al., "Evaluation of a laser based structured light system for 3D reconstruction of underwater environments," 5th MARTECH International Workshop on Marine Technology (2013); see also Payeur et al., "Dense stereo range sensing with marching pseudorandom patterns," Fourth Canadian Conference on Computer and Robot Vision (2007); see also Fernandez et al., "Absolute phase mapping for one-shot dense pattern projection," IEEE Computer Society Conference on Computer Vision and Pattern Recognition Workshops (2010); and see Sarafraz et al., "A structured light method for underwater surface reconstruction. *ISPRS J. Photogramm. Remote Sens* (2016). Other variations may include two or more cameras at various angles to improve accuracy or to compensate for the directionality of the pattern. See e.g. Ishii, "High-speed 3D image acquisition using coded structured light projection," in *IEEE RSJ International Conference on Intelligent Robotics and Systems* (2007); see also Huang et al., "Fast three-step phase-shifting algorithm," *Appl. Opt* 45 (2006); see also Bruno et al., "Experimentation of structured light and stereo vision for underwater 3D reconstruction," *ISPRS J. Photogramm. Remote Sens* 66(4) (2011). Different patterns may be projected sequentially and then stitched together to form a point cloud. The resolution of the resultant point cloud is limited by the resolution and complexity of the projected pattern.

Another method of robot vision is based on a technique called visual odometry, which determines the position and orientation of a robot by analyzing associated camera images. Images are acquired using either a single camera or multiple cameras working in stereo or omnidirectional cameras. Visual odometry can generally be done at a fraction of the cost and computing power of other robot vision methods and has been studied extensively. See e.g. Campbell et al., "A robust visual odometry and precipice detection system using consumer-grade monocular vision," IEEE International Conference on Robotics and Automation (2005); see also Irani et al., "Recovery of ego-motion using image stabilization," 1994 *IEEE Computer Society Conference on Computer Vision and Pattern Recognition* (1994); see also Burger et al., "Estimating 3-D egomotion from perspective image sequences," *IEEE Trans. Pattern Anal. Mach. Intell* 12(11) (1990); see also Jaegle et al., "Fast, robust, continuous monocular egomotion computation," *IEEE International Conference on Robotics and Automation* (2016); see also Botelho et al., "Visual odometry and mapping for underwater autonomous vehicles," *6th Latin American Robotics Symposium* (2009); and see Shakernia et al., "Omnidirectional egomotion estimation from back-projection flow," *IEEE Conference on Computer Vision and Pattern Recognition* (2003).

As is well understood, the way light interacts with the ocean is peculiar and has been studied for decades. Light changes as it enters the water and as it travels to the depths it continues to change. This has a marked effect on colors as light attenuates due to absorption and scattering. Absorption is of particular interest because light at different wavelengths experiences higher or lower absorption over the same distance. For example, red light is absorbed over a short distance and may only travel up to 10 m through clear salt water, whereas green light may travel up to 25 times as far before it is absorbed. As a result, underwater photography and videography frequently requires additional light sources or filters to restore visible wavelengths of light to compensate for the absorption. The absorption of light in water is generally described by the Beer-Lambert law:

$$I_d = I_O e^{-\alpha d}$$

where $I_d$ represents the intensity of the light at a given distance d and $I_O$ represents the intensity of the light at the source. The absorption coefficient is represented by $\alpha$. This represents an exponential decay proportional to the distance and absorption coefficient for a given wavelength. The absorption coefficient can be corrected for temperature and salinity, as:

$$\Phi = \alpha + \Psi_T(T-273.15) + \Psi_s C_s,$$

where $\Psi_T$ is a wavelength dependent temperature dependence, $\Psi_s$ is a salinity dependence, T is a temperature in degrees Kelvin, and $C_s$ is a salinity. For example, for a wavelength of 620 nm in salt water, the temperature dependence $\Psi_T$ is about 0.000539 m$^{-1\circ}$ C.$^{-1}$ and the salinity dependence $\Psi_T$ is 0.0000838 m$^{-1}$g$^{-1}$L. Utilizing the temperature and salinity corrected absorption coefficient $\Phi$, the Beer-Lambert expression can be rearranged to express a distance d as:

$$d = -\left(\frac{1}{\Phi}\right)\ln\left(\frac{I_d}{I_O}\right)$$

Additionally, it is understood that color may be expressed as RGB values. The RGB values are related to three standard primaries called X, Y, and Z by the International Commission on Illumination or Commission Internationale de l'Éclairage (CIE). The XYZ color space is an international standard used to define colors invariant across devices. The primaries are correlated to specific wavelengths of light. This comparison links the physical pure colors to physiological perceived colors and defines the XYZ color space and the RGB color space. The RGB color space varies between devices as a local device's interpretation of the XYZ color space standard. Typically some portion of the color space comprises a color triangle and (x,y) values correlate with corresponding RGB values between zero and one. Each red, green, and blue value that makeup a color is typically stored as an 8-bit byte for most devices, although higher resolution is available on some devices. A one corresponds to 255, and each corner is represented as (255,0,0) "red," (0,255,0) "green," and (0,0,255) "blue." For every fraction of each of these values there is a corresponding wavelength of color. For example, a wavelength of 620 nm corresponds to an RGB value of (255,0,0) or (1,0,0), the brightest red. "Brightest" may be misleading and refers to the shade of red and not the typical brightness. The combination of RGB values generally indicate the color at a pixel in a digital imaging device.

It would be advantageous to provide a robot vision system using digital imaging devices to distinguish relative distances between objects in a captured image. It would be particularly advantageous if such a system could provide the relative distances in a passive manner without requiring an emission such as a laser light or a sound ping, by simply collecting images and estimating the attenuation of reflected light. It would be additionally advantageous if such a system could estimate the attenuation of reflected light using understood camera filtering techniques combined with an existing standard such as an RGB color triangle. Such relative distances passively sensed from captured images of a surrounding environment could be utilized to provide a 3D point cloud of the surrounding environment, greatly enhancing the ability of a robotic vision system to ascertain surroundings for the purpose of navigation.

These and other objects, aspects, and advantages of the present disclosure will become better understood with reference to the accompanying description and claims.

SUMMARY

The apparatus and method disclosed provides a robot vision apparatus comprising an imaging apparatus with one or more digital cameras, a camera filter, and a filter mechanism mechanically configured to position the camera filter within a field of view of one of the one or more cameras. The robot vision apparatus further comprises a digital processor in data communication with the imaging apparatus for receipt of unfiltered and filtered images captured by the one or more cameras.

A processor is in data communication with the imaging apparatus comprising the one or more cameras and is programmed to direct the imaging apparatus capture unfiltered and filtered images of an object and generate an unfiltered pixmap and a filtered pixmap of the object. The pixmaps generated comprise a plurality of pixels with each pixel comprising a pixel value referenced to a color table, and the color table defining a plurality of colors. Each color is referenced by the color table to at least a first primary color and a second primary color using a first color space coordinate and second color space coordinate. Typically the color table utilizes at least three primary colors, such as red, green, and blue. The processor receives the unfiltered and filtered pixmaps and conducts pixel matching of the unfiltered and filtered pixmaps to determine match pairs. Each match pair comprises a specific unfiltered pixel and specific filtered pixel which represent the same scene point in the unfiltered and filtered images. The processor assigns an (x,y) pair coordinate to the match pair based on a location of the specific unfiltered pixel in the unfiltered pixmap and a location of the specific filtered pixel in the filtered pixmap. The processor further determines an image distance for the match pair by extracting an unfiltered first color space coordinate $R_u$ from the specific unfiltered pixel of the match pair and a filtered first space coordinate $R_f$ from the specific filtered pixel of the match pair, where the first color coordinates correspond to the first primary color of the color space utilized. The processor determines the image distance for the match pair using the unfiltered and filtered first color space coordinates and an absorption coefficient value, with an expression such as $d_r = -(1/\Phi)\ln(R_u/R_f)$. The processor subsequently generates a data point in a coordinate system having at least three dimensions, by using the (x,y) pair coordinate of the match pair to define coordinates in the first and second dimensions the determined image distance to define a coordinate in the third dimension. The processor determines an image distance for each match pair in order to generate the point cloud representing the object or objects in the unfiltered and filtered images.

The novel apparatus and principles of operation are further discussed in the following description.

Figure 1:
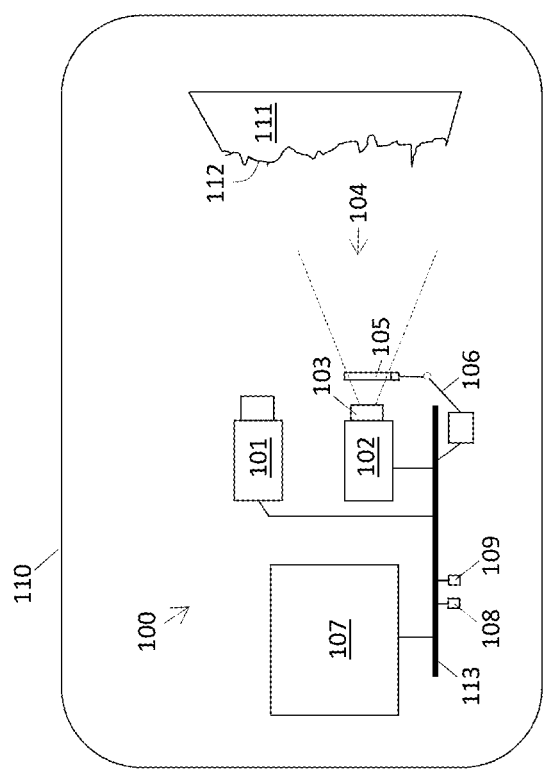
FIG. 1 illustrates a particular embodiment of the robot vision apparatus.

Embodiments in accordance with the invention are further described herein with reference to the drawings.

DETAILED DESCRIPTION OF THE INVENTION

The following description is provided to enable any person skilled in the art to use the invention and sets forth the best mode contemplated by the inventor for carrying out the invention. Various modifications, however, will remain readily apparent to those skilled in the art, since the principles of the present invention are defined herein specifically to provide an apparatus and method for generating a 3D point cloud representing an object by comparison of an unfiltered and filtered image of the object.

The disclosure provides an apparatus and method allowing a robot vision system to generate a 3D point cloud of a surrounding environment through comparison of captured images of the surrounding environment. The apparatus and method operates in some medium such as water, typically seawater, and captures both a unfiltered image of a particular scene and a filtered image of the particular scene using one or more digital cameras. The filtered image is captured using a camera filter which tends to pass certain wavelength bandwidths while mitigating the passage of other bandwidths. A processor receives the unfiltered and filtered images, pixel matches the unfiltered and filtered images, and determines an image distance for each pixel based on comparing the color coordinates determined for that pixel in the unfiltered and filtered image. The color coordinates compared in the unfiltered and filtered images correspond to the one or more specific wavelengths of light which tend to be passed by the camera filter.

The image distance determined provides a relative distance from the digital camera to an object or object portion based on providing a relative measure of the amount of attenuation that light reflected from the object or object portion experiences while transited through a medium to the digital camera. As noted above, the Beer-Lambert law can be utilized to specify a distance based on the amount of attenuation which has occurred. However, determination of this distance requires knowledge of an intensity $I_o$ at the object itself. The apparatus and method disclosed here avoids the $I_o$ requirement and provides a relative measure of attenuation determined by comparing a pixel in an unfiltered image with a corresponding pixel in a filtered image. The difference in the amount of attenuation provides an image distance for the pixel, and the relative magnitude of all image distances determined for all pixels in the unfiltered and filtered images allows generation of a 3D point cloud representing the object captured in the unfiltered and filtered images.

The apparatus and method makes use of the distance expression of the Beer-Lambert law noted above, and utilizes pixel data as representative of luminosity. For an unfiltered pixel comprising an unfiltered pixmap of an image, where the unfiltered pixel provides an unfiltered color coordinate $R_u$, an unfiltered distance $d_u$ may be represented as:

$$d_u \approx -\left(\frac{1}{\Phi}\right)\ln\left(\frac{R_u}{R_O}\right)$$

where $R_O$ is based on conditions at the object itself. Similarly, for a corresponding filtered pixel comprising a filtered pixmap of an image, where the filtered pixel provides an filtered color coordinate $R_f$, an filtered distance $d_f$ may be represented as:

$$d_f \approx -\left(\frac{1}{\Phi}\right)\ln\left(\frac{R_f}{R_O}\right)$$

The difference in the two distances expressed as above provides the image distance $d_r$ for the pixel, expressed as:

$$d_r = -\left(\frac{1}{\Phi}\right)\left(\ln\left(\frac{R_u}{R_o}\right) - \ln\left(\frac{R_f}{R_o}\right)\right)$$

$$= -\left(\frac{1}{\Phi}\right)([\ln(R_u) - \ln(R_o)] - [\ln(R_f) - \ln(R_o)])$$

$$= -\left(\frac{1}{\Phi}\right)\ln\left(\frac{R_u}{R_f}\right) \rightarrow d_r \propto \ln\left(\frac{R_u}{R_f}\right) \text{ for a given } \Phi$$

Pixel matching of the unfiltered and filtered images provides correspondence between unfiltered and filtered pixels of the unfiltered and filtered images, and use of respective color coordinate information $R_u$ and $R_f$ provided by the two pixels allows determination of the image distance $d_r$ for the match pair of pixels. Using an (x, y) location assigned to the match pair of pixels during the pixel matching process and the image distance $d_r$ determined, a data point can be generated in a 3D point cloud. Conducting this process for all match pairs which result from the pixel matching generates a 3D point cloud representative of the object or objects captured in both the unfiltered and filtered images, with the image distances reflecting relative distances from the digital camera for each object or object portion captured by the pixels of the match pair. As discussed further below, pixel matching may be conducted using algorithms known in the art for such purpose, or in some embodiments may be conducted by ensuring a high degree of alignment between unfiltered and filtered fields-of-view during capture of the respective images.

In typical embodiments, the color coordinates for each pixel in the unfiltered and filtered pixels are expressed as coordinates in a Red-Green-Blue (RGB) color triangle and the camera filter tends to allow passage of red wavelength bandwidths while mitigating passage of blue and green wavelength bandwidths. Comparison of the red color coordinates of the unfiltered and filtered images provides a measure of the attenuation of red wavelengths that occur between the object imaged and the digital camera for each pixel allowing calculation of the image distance for the pixel and generation of a point cloud in a three dimensional coordinate space to serve as a representation of the object or objects captured.

A particular embodiment of the robot vision system and apparatus is illustrated at FIG. 1 and generally indicated by 101. In this embodiment, robot vision apparatus 100 comprises an imaging apparatus comprising one or more digital cameras such as digital camera 101 and digital camera 102. The one or more cameras comprises a specific camera comprising a lens having a field of view, such as digital camera 102 with lens 103 having a field of view generally indicated by 104. The imaging apparatus of robot vision 100 further comprises a camera filter 105 and a filter mechanism 106 where filter mechanism 106 is mechanically configured to position camera filter 105 in a filtering position where camera filter 105 is within the field of view of one of the one or more digital camera, such as field of view 104 of digital camera 102 at FIG. 1. Robot vision apparatus 100 further comprises a digital processor 107 in data communication with the imaging apparatus. In certain embodiments, at least the one or more cameras such as 101 and 102, processor 107, and filter mechanism 106 are fixably attached to platform 113. In other embodiments, robot vision apparatus 100 is surrounded by a volume of water.

Each of the one or more digital cameras are programmed to capture an image and generate a pixmap of the image. For example at FIG. 1, both digital camera 102 and digital camera 103 are programmed to capture an image such as some portion of the face 112 of an object 111. The pixmap generated by each of digital cameras 102 and 103 comprises a plurality of pixels with each pixel comprising a pixel value which references to a color table. The color table or palette defines a plurality of colors using the pixel value and referenced to at least a first primary color and a second primary color by a first color space coordinate and second color space coordinate respectively. Typically the color table utilizes at least three primary colors and the pixel values reference to a color table describing an color triangle, where (X, Y, Z) color space coordinates within the color triangle provide a coordinate for the first, second, and third primary color and represent corresponding wavelengths comprising a spectrum of color. Thus, the primary colors established by the pixmap and interpreted by the color table represent specific wavelength bandwidths of light sensed by the one or more cameras. For example, a first primary color might represent light received having a bandwidth from 590 nm to 750 nm, a second primary color might represent light received having a bandwidth from 495 nm to 590 nm, and a third might represent light received having a bandwidth from 380 nm to 495 nm. The pixmap generated thereby defines a composite color of each pixel by establishing the amount of each primary color present in the intensity of each pixel, and effectively specifies the amount of each primary color to be additively provided to produce a composite color for the pixel. Typically the pixmap is an ordered set of values where the composite color for each pixel is specified as an individual set in the ordered set, and the location of a pixel relative to other pixels in the color image is determined by its position in the ordered set.

Additionally, camera filter 105 has a Full Width at Half Maximum (FWHM) bandwidth and tends to allow passage of light wavelengths within the FWHM and mitigate passage of light wavelengths outside the FWHM. At FIG. 1, camera filter 105 possesses an FWHM which tends to pass one or more specific light wavelengths within the first wavelength bandwidth of the first primary color utilized by the pixmap and tends to mitigate passage of wavelengths within at least the second primary color utilized by the pixmap. Correspondingly, an filtered image taken by a specific digital camera through filter 105 of an object such as 111 will generate a filtered pixmap generally having a proportionally greater representation of the one or more specific light wavelengths relative to wavelengths outside the FWHM bandwidth, as compared to an unfiltered pixmap generated by a digital camera without digital filter 105. The apparatus of FIG. 1 utilizes this distinction in order to generate a 3D point cloud of an object such as face 112 of object 111.

Figure 2:
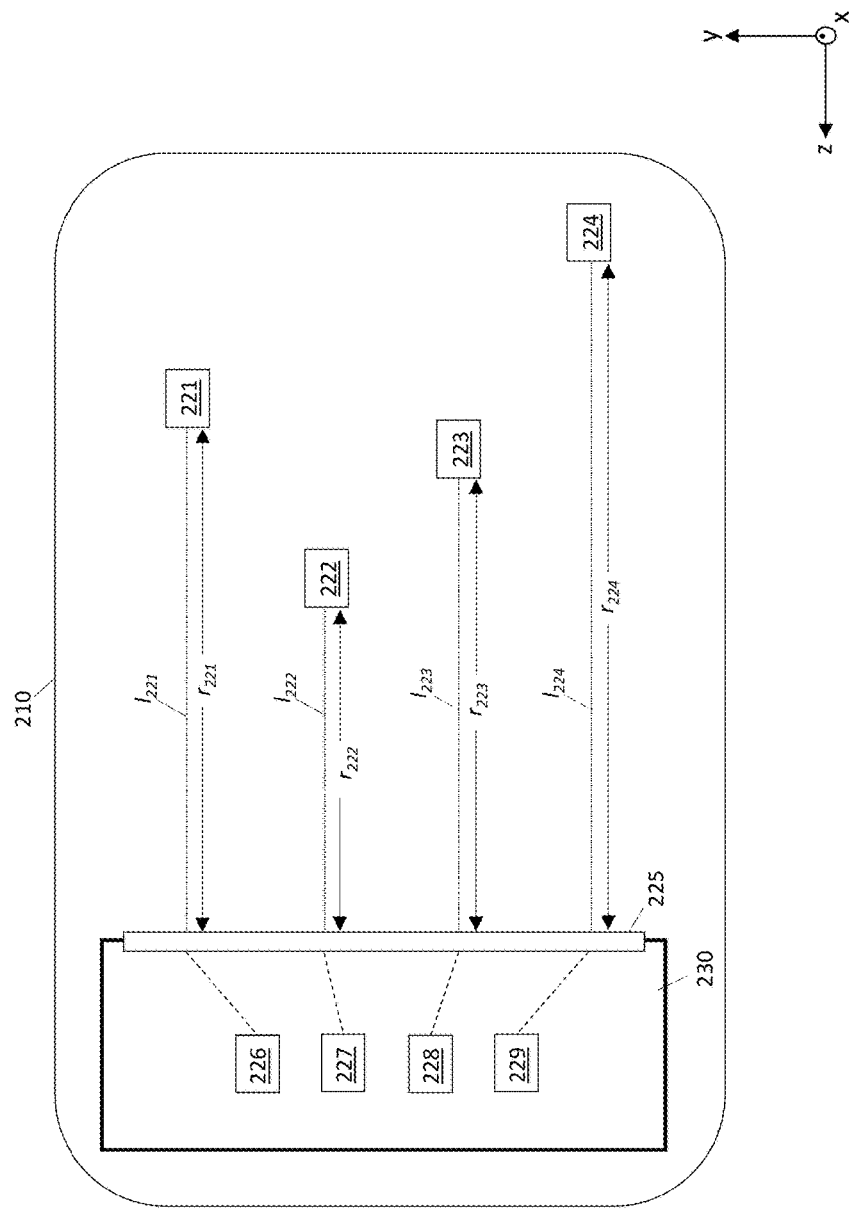
FIG. 2 illustrates another embodiment of the robot vision apparatus.

As discussed, light traveling through an environment such as a volume 110 from, for example, face 112 to lens 103 of digital camera 102, will experience attenuation as it travels through the environmental media within volume 110. Higher wavelengths experience a greater degree of attenuation, producing a color shift as the light travels. For example, wavelengths typically associated with colors blue and green experience a significantly slower exponential decay than those associated with red, resulting in a color shift toward blue-green as light travels through the environment. Providing a measure of the degree of that shift can provide a distance between objects in an image. Correspondingly, the difference in red pixel values between two images, one filtered and the other unfiltered, taken at generally the same location or when subsequently pixel matched, may be used to determine relative distances between objects within the frame, allowing for generation of a 3D point cloud representing the objects or features imaged. For example, FIG. 2 illustrates four features 221, 222, 223, and 224 in a volume of water 210. Reflected light from each of the features impacts a camera lens 225 comprising a digital camera 230, with the reflected light from each feature illustrated as $l_{221}$, $l_{222}$, $l_{223}$, and $l_{224}$ for features 221, 222, 223, and 224 respectively. The light travels through the media of volume 210 over distances illustrated as $r_{221}$, $r_{222}$, $r_{223}$, and $r_{224}$. For ease of illustration the reflected light is illustrated as effectively parallel. In the example at FIG. 2, the reflected light for each feature is captured by digital camera 230 and pixel data representing each feature is generated in the pixels illustrated, with pixel 226 corresponding to feature 221 and $l_{221}$, pixel 227 corresponding to feature 222 and $l_{222}$, pixel 228 corresponding to feature 223 and $l_{223}$, and pixel 229 corresponding to feature 224 and $l_{224}$. The pixel data generated comprises information describing the relative presence or absence of various light wavelengths in the reflected light and is sufficient to represent the reflected light using a plurality of primary colors, typically at least three. For example and as is known in the art, the pixel data generated might comprise a pixel value which can be subsequently applied to a look up table describing a color map and providing relative values for each of the primary colors. Typical applications use an RGB color triangle with red, green, blue primary colors and the corners of the triangle denoted as (255,0,0) for red, (0,225,0) for green, and (0,0, 225) for blue, with color space coordinates specified within those corners representing corresponding wavelengths comprising a spectrum of color. See e.g. K. Plataniotis and A. Venetsanopoulos, *Color Image Processing and Applications* (2000), among many others.

The apparatus and system disclosed acts to determine relative distances from digital camera 230 among the features without foreknowledge of any of $r_{221}$, $r_{222}$, $r_{223}$, or $r_{224}$ based on comparison of filtered and unfiltered pixel data in corresponding images. For example at FIG. 2, following capture of an unfiltered image by digital camera 230, pixel 227 might generate pixel data which translates the reflected light $l_{221}$ though a color map as ($R_{221}$, $G_{221}$, $B_{221}$) and, following capture of a filtered image, generate pixel data which translates the reflected light $l_{221}$ though the color map as ($R_{221}'$, $G_{221}'$, $B_{221}'$). In both images, each of the various wavelengths represented by the pixel data will have experienced some degree of attenuation during transit through the environmental media of volume 210. However, the evidence of attenuation for light wavelengths within the FWHM of the camera filter is heightened by the comparison of the unfiltered and filtered images, and effectively provides a representation of a relative range to an object as compared to other objects in the image, based on the degree of attenuation evidenced from each pixel.

The degree of attenuation evidenced from each pixel may be evaluated using a relationship based on the rearranged Beer-Lambert law as previously discussed. For feature 221, the image distance may be expressed as $d_{r(221)} = -(1/\Phi)\ln(R_{221}/R_{221}')$. A similar determination for feature 222 with unfiltered ($R_{222}$, $G_{222}$, $B_{222}$) and filtered ($R_{222}'$, $G_{222}'$, $B_{222}'$) pixel values obtained through pixel 227 would provide $d_{r(222)} = -(1/\Phi)\ln(R_{222}/R_{222}')$. Because $l_{222}$ experiences less attenuation of the FWHM wavelengths compared to $l_{221}$, due to $r_{222}$ being less than $r_{221}$, and because the attenuation is a function of distance traveled, the relationship between the resulting $d_{r(221)}$ and $d_{r(222)}$ provides a relative measure of the difference between $r_{221}$ and $r_{222}$, and correspondingly provides a relative measurement of the relative distances of features 221 and 222 from digital camera 230. Similar determinations can be conducted for features 223 and 224 using pixels 228 and 229 respectively, producing a measure of the relative distances among all of features 221, 222, 223, and 224. This information may be used to generate a point cloud in an x-y-z coordinate system such as that shown using, for example, the unfiltered/filtered pixel location for the x and y coordinate and the resulting image distance $d_r$ for the z coordinate.

It is understood that the absorption coefficient value Φ may be specifically quantified and utilized for determination of relative image distances such as $d_{r(221)}$ and $d_{r(222)}$ as exemplified above, however given that the point cloud ultimately generated as a result of the image distances is based on determining relative distances between objects, the absorption coefficient value Φ may have any constant value (including equal to one), and the relative spatial relationships reflected among the various objects will be preserved. Any absorption coefficient value Φ may be utilized within this disclosure in order to estimate relative distances and construct a 3D point cloud representing the spatial relationship of various features or objects captured in an unfiltered image and a filtered image. However, in certain situations, such as for example when the 3D point cloud generated is intended to be utilized as a navigation tool for a platform such as an underwater vehicle, it may be advantageous to base the absorption coefficient value Φ on a surrounding medium.

Figure 3:
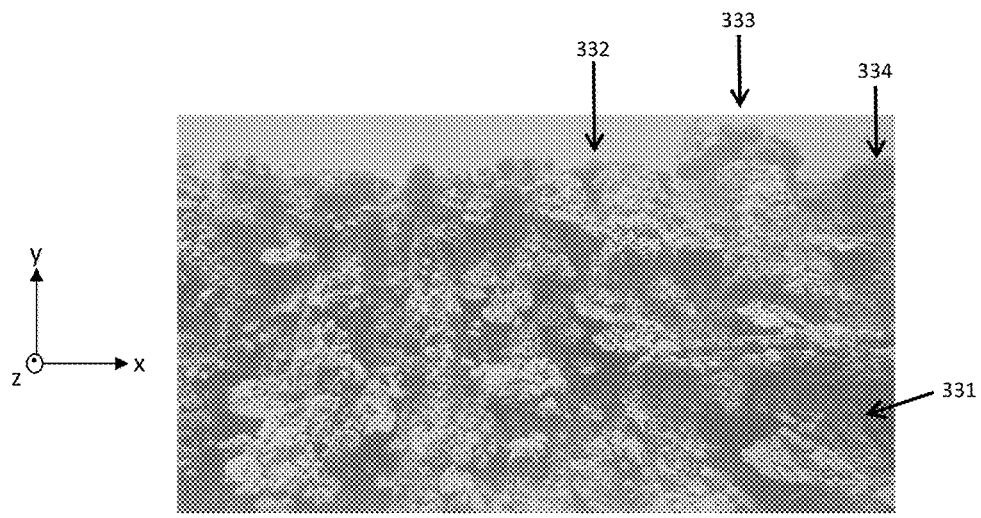
FIG. 3 illustrates an image of the first object.
Figure 4:
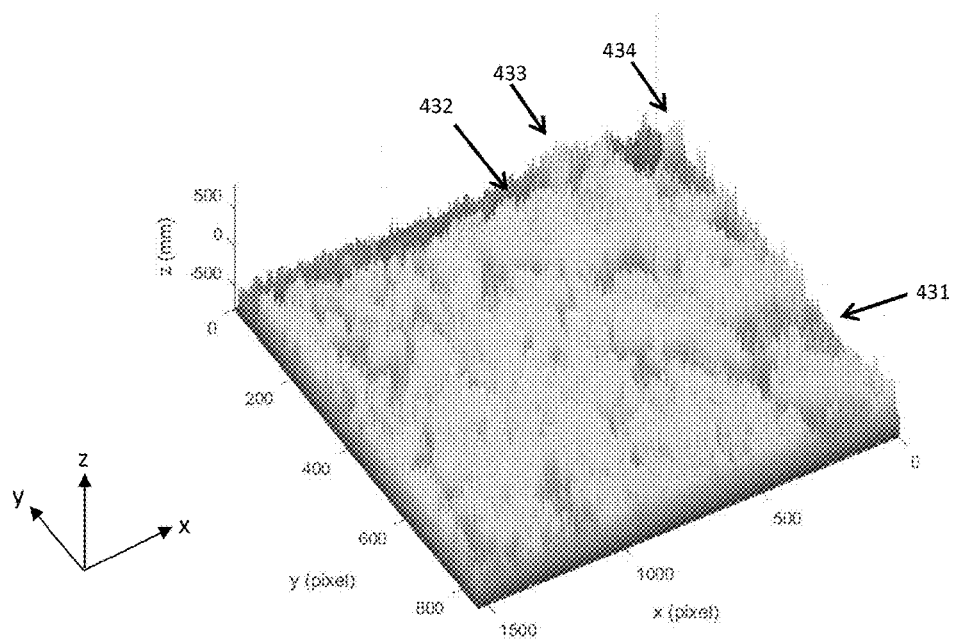
FIG. 4 illustrates a 3D point cloud of the first object.

The apparatus and system disclosed conducts the methodology outlined above using a processor such as processor 107 at FIG. 1. Processor 107 is in data communication with the imaging apparatus comprising the one or more cameras and directs the imaging apparatus to generate an unfiltered pixmap of an object and a filtered pixmap of the object, receives the unfiltered and filtered pixmaps, conducts pixel matching of the unfiltered and filtered pixmaps to generate match pairs, then determines an image distance for each match pair using a method similar to the above. Processor 107 subsequently utilizes the image distances and an (x,y) coordinate of the match pair to generate a point cloud representing the object. An exemplary example discussed further below is shown at FIGS. 3 and 4, where FIG. 3 shows a photograph of an object surface with features generally indicated by 331, 332, 333, and 334 having locations in accordance with the x-y-z axis illustrated, and FIG. 4 shows a point cloud and corresponding features 431, 432, 433, and 434 generated by unfiltered and filtered pixel comparisons and calculation of image distances as described, with locations in accordance with the x-y-z axis illustrated.

Processor 107 works in conjunction with the imaging apparatus which, as discussed, comprises one or more digital cameras such as 101 and 102, and further comprises a camera filter 105. The one or more digital cameras may comprise a single digital camera where camera filter 105 is moved into and out of its field-of-view by filter mechanism 106, or may comprise two or more digital cameras where filter mechanism 106 maintains filter 105 in a substantially fixed position within the field-of-view of a specific camera, or some combination of the two arrangements. Each digital camera is programmed to capture an image and generate a pixmap, where the pixmap comprises a plurality of pixels, with each pixel comprising a pixel value referenced to a color table that provides at least a first primary color and a second primary color using a first color space coordinate and a second color space coordinate. Further, camera filter 105 has a FWHM bandwidth such that one or more specific light wavelengths are both within the wavelength bandwidths represented by the first primary color and also within the FWHM bandwidth of the camera filter. In a typical embodiment, the first primary color represents a band of wavelengths generally greater than the band of wavelengths represented by the second primary color. Further in certain embodiments, the color table additionally provides a third primary color and defines coordinates in a color space such an RGB color space. The color space is typically an additive color space, as is known in the art.

Figure 5:
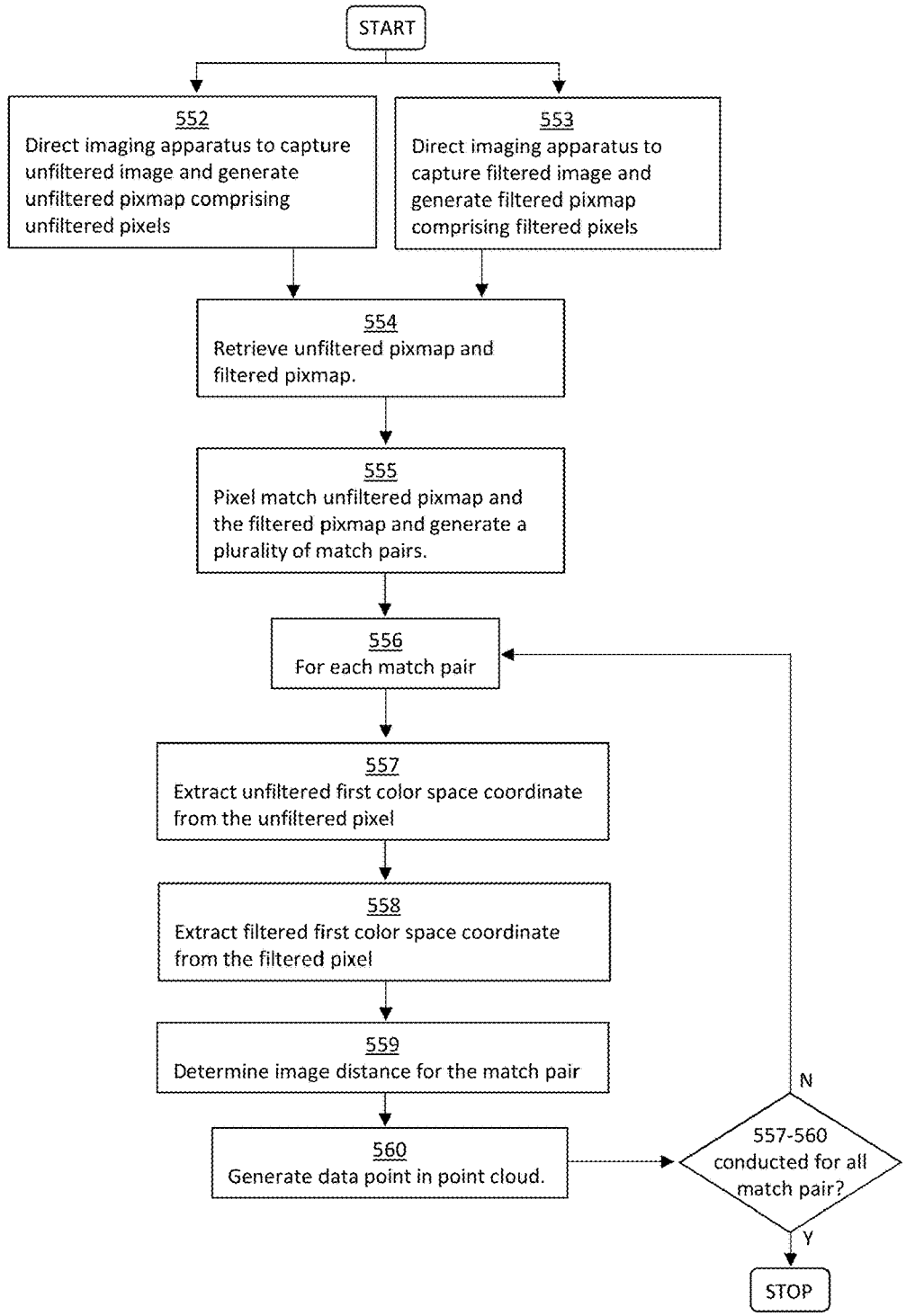
FIG. 5 illustrates an embodiment of a process conducted by a processor comprising the robot vision apparatus.

An embodiment of the process through which Processor 107 generates a point cloud is illustrated at FIG. 5 and commences at START. At step 552, processor 107 directs the imaging apparatus to capture an unfiltered image of an object using an individual camera having a field-of-view clear of camera filter 105. The individual camera captures the unfiltered image and generates an unfiltered pixmap comprising a plurality of unfiltered pixels. Each unfiltered pixel comprises an unfiltered pixel value which references to the color table, and thereby provides information allowing determination of an unfiltered first color space coordinate which represents the first primary color in the unfiltered pixel. At step 553, processor 107 directs the imaging apparatus to capture an filtered image of an object using a specific camera and with camera filter within the field-of-view of the specific camera. In certain embodiments, the imaging apparatus utilizes filter mechanism 106 to place camera filter 105 within the field-of-view of the specific camera, while in other embodiments, filter mechanism 106 constantly maintains camera filter 105 within the field-of-view of the specific camera. The specific camera captures the filtered image and generates a filtered pixmap comprising a plurality of filtered pixels. Similar to before, each filtered pixel comprises a filtered pixel value which references to the color table, and thereby provides information allowing determination of an filtered first color space coordinate which represents the first primary color in the filtered pixel. At step 554, processor 107 retrieves the unfiltered pixmap comprising the unfiltered pixels and the filtered pixmap comprising the filtered pixels from the imaging apparatus. It is understood that steps 552 and 553 may be conducted in any order in order to generate the unfiltered and filtered pixmaps.

At step 555, processor 107 conducts pixel matching of the unfiltered pixmap and the filtered pixmap in order to associate each specific unfiltered pixel comprising the unfiltered pixmap with a specific filtered pixel comprising the filtered pixmap, and generate a plurality of match pairs. Generally, the pixel matching explicitly matches the unfiltered pixels comprising the unfiltered image and the filtered pixels comprising the filtered image and correspondence is encoded in a match sequence, where each match is an ordered pair of pixels signifying that the respective pixels represent the same scene point in the unfiltered and filtered images. Such pixel matching methods and the generation of match pairs are known in the art. See e.g. Chen et al., "Pixel-Based Correspondence and Shape Reconstruction for Moving Objects," 2009 *IEEE 12th International Conference on Computer Vision Workshops, ICCV Workshops* (2009); see also Yaguchi et al., "Full Pixel Matching between Images for Non-linear registration of objects," *Information and Media Technologies* 5(2) (2010); see also Takita et al, "A Sub-pixel correspondence search technique for computer-vision applications," *IEICE Trans. Fundamentals* 87(8) (2004); see also Uchida et al., "Fast and Accurate Template Matching using Pixel Rearrangement on the GPU," 2011 *Second International Conference on Network-*

*ing and Computing* (2011). Processor 107 determines the specific unfiltered pixels and specific filtered pixels which represent the same scene point in the unfiltered and filtered images and assigns an (x,y) pair coordinate to the match pair based on a location of the specific unfiltered pixel in the unfiltered pixmap and a location of the specific filtered pixel in the filtered pixmap. Processor 107 generates a plurality of match pairs through this process. Processor 107 may generate the plurality of match pairs using any appropriate methodology whereby an unfiltered pixel of an unfiltered image and a filtered pixel of a filtered image location of a filtered pixel are associated into a match pair and provided with an (x,y) pair coordinate.

At step 556, processor 107 generates the point cloud by conducting a series of steps for each matched pair. At 557, processor 107 extracts an unfiltered first color space coordinate from the unfiltered pixel of the matched pair, and at step 558, extracts a filtered first color space coordinate from the filtered pixel of the matched pair. For example, where an unfiltered pixel in a match pair provides an unfiltered pixel value translating to $(R_i, G_i, B_i)$ in an RGB color space and a filtered pixel in a match pair provides a filtered pixel value translating to $(R_i, G_i, B_i)$ in the RGB color space, and where $R_i$ and $R_i'$ represent the band of wavelengths of the first primary color, processor 107 extracts $R_i$ as the unfiltered first color space coordinate for the matched pair and $R_i'$ as the filtered first color space coordinate for the matched pair.

Subsequently, at step 559, processor 107 determines an image distance for the match pair using the unfiltered first color space coordinate and filtered first color space coordinate. Processor 107 determines the image distance using a difference between a logarithm of a first term and a logarithm of a second term, where the first term comprises the unfiltered first color space coordinate of the each match pair such as $R_i$ and the second term comprises the filtered first color space coordinate of the each match pair such as $R_i'$. The difference may be determined by establishing the logarithmic values separately and subtracting, or by determining a logarithm of a ratio, or any other appropriate mathematical operations known in the art. In a particular embodiment, and for each match pair, a value $\Delta R$ is equal to a scaling factor F times a difference between a logarithm of the unfiltered first color space coordinate and a logarithm of the filtered first color space coordinate, where the scaling factor F is a constant value over all match pairs, and the difference between the logarithm of the first term and the logarithm of the second term divided by the value $\Delta R$ is greater than 0.75 and less than 1.25 in some embodiments, greater than 0.85 and less than 1.15 in other embodiments, and greater than 0.95 and less than 1.05 in further embodiments. For example, in certain embodiments, the value $\Delta R$ is equal to $F \times \ln(R_i/R_i')$ where the scaling factor F is some constant for all match pairs, and image distance $d_r$ is determined as $\ln(x_i/x_i')$, where $x_i$ comprises $R_i$ and $x_i'$ comprises and $0.75 \leq (d_r/\Delta R) \leq 1.25$ in a first embodiment, $0.85 \leq (d_r/\Delta R) \leq 1.15$ in a second embodiment, and $0.95 \leq (d_r/\Delta R) \leq 1.05$ in an additional embodiment.

At 560, processor 107 generates a data point in a coordinate system having at least three dimensions, by using the (x,y) pair coordinate of the match pair to define coordinates in the first and second dimensions the determined image distance to define a coordinate in the third dimension.

Processor 107 conducts steps 557-560 for each match pair in the plurality of match pairs until, at STOP, processor 107 has generated the representative point cloud in the coordinate system based on the unfiltered and filtered images of the object.

At step 554, processor 107 may receive unfiltered and filtered pixel values where the pixel values reference to a color table with processor 107 subsequently extracting the first color coordinate by converting the pixel values using the color table. Alternately, processor 107 may receive unfiltered and filtered pixels in a data form where conversion using the color table has already occurred, for example in the one or more cameras. The specific data form of the unfiltered and filtered pixels received is not limiting within this disclosure, provide the unfiltered and filtered pixels provide information allowing extraction of an unfiltered first color space coordinate and a filtered first color space coordinate.

In some embodiments, processor 107 determines an absorption coefficient value and subsequently determines the image distance using the difference between the logarithm of the first term and the logarithm of the second term and using the absorption coefficient value. In typical embodiments, the absorption coefficient value is determined for a specific light wavelength that is within the wavelength bandwidths represented by the first primary color and also within the FWHM bandwidth of the camera filter. Processor 107 may obtain the absorption coefficient from memory, or may provide some assessment of its environment and determine a corrected absorption factor. In certain embodiments, robot vision apparatus 100 is intended for use in a water environment and includes temperature detector 108 and salinity detector 109 in data communication with processor 107, in order for processor 107 to conduct temperature and salinity corrections.

In certain embodiments, the first wavelength bandwidth of the first primary color comprises a first center wavelength and the second wavelength bandwidth of the second primary color comprises a second center wavelength, and the first center wavelength is greater than the second center wavelength, such that the unfiltered and filtered images accentuate attenuation of higher wavelength light. Such an approach may increase the relative accuracy of the image distances obtained. In other embodiments, the first wavelength bandwidth and the second wavelength bandwidth each comprise one or more wavelengths in a visible spectrum, such as from about 390 nm to about 700 nm.

In a further embodiment, the color space described by the color table comprises representations for at least a first primary color, a second primary color, and a third primary color, and the color table defines a color coordinate comprising a first color space coordinate corresponding to the first primary color, a second color space coordinate corresponding to the second primary color, and a third color space coordinate corresponding to the third primary color. In other embodiments, the color space is an additive color space. In additional embodiments the color space is an Red-Green-Blue (RGB) color space defined by the three chromaticities of the red, green, and blue additive primaries.

The disclosure further provides a method of generating a point cloud in a coordinate system by obtaining one or more digital cameras programmed to capture an image and generate a pixmap of the image comprising a plurality of pixels, capturing an unfiltered image of an object and generating an unfiltered pixmap, and capturing a filtered image of the object and generating a filtered pixmap using a specific digital camera having camera filter within its field of view and between the specific digital camera and the object. The method further comprises communicating the unfiltered pixmap and the filtered pixmap to a processor, where the processor is programmed to perform steps in the manner described above and comprising pixel matching the unfiltered pixmap and the filtered pixmap and generating a plurality of match pairs, extracting an unfiltered first color space coordinate and a filtered first color space coordinate from each matched pair, determining an image distance for the each match pair using a difference between a logarithm of a first term and a logarithm of a second term, and generating a data point for the each match pair using the (x,y) pair coordinate assigned to the each match pair the image distance for the each match pair.

EXEMPLARY EMBODIMENTS

In the exemplary embodiments discussed below all images were collected using the sale camera setup in the same general location by the same operator over consecutive days, with all processing done on the same computer using the same version of software.

As discussed, the natural properties of light may be used to compare two underwater images to provide a three-dimensional representation of the environment. If wavelength-specific luminous intensities can be obtained at both an object and at a camera, then the distance from the subject to the camera $d_B$ can be determined through the Beer-Lambert law by:

$$d_B = -\left(\frac{1}{\Phi}\right)\ln\left(\frac{I_B}{I_{o(B)}}\right)$$

where $\Phi$ is a corrected absorption coefficient, $I_{O(B)}$ is a wavelength-specific luminous intensity at the object, $I_B$ is a wavelength-specific luminous intensity of light reflecting off the object and arriving at the camera, and $d_B$ is the distance between the object and the camera. As discussed, light intensity at different wavelengths experience different exponential decays and is perceived as a shift in color from reds to blues and greens. Correspondingly, as light travels through a medium such as water from the object to the camera, RGB values captured by the camera decay toward the green-blue side of the color triangle. An observer, or in this case a camera, sees a different color because the wavelength-specific luminous intensities decay unevenly causing the color shift. As the red is absorbed first there is a shift in color towards blue and green. This shift in color provides a measure of the shift in luminous intensities.

In the embodiments discussed herein, the difference in red pixel values between two images, one filtered and the other unfiltered, taken at the same location, are used as an indication of relative distance between objects within the frame. Substituting filtered and unfiltered red pixel values for initial and final intensities into the relationship above provides:

$$d_B = -\left(\frac{1}{\Phi}\right)\ln\left(\frac{R_u}{R_f}\right)$$

where $R_u$ represents the R matrix in the unfiltered image, $R_f$ is the R matrix in the filtered image, and $d_B$ has been replaced with $d_r$ to denote a relative distance between objects within the image. A boundary condition occurs when the filtered pixel value contains no red (0,0,0) because taking the natural log of 0 yields $-\infty$. This generally indicates that either there is no red reflected from the object (the initial intensity for red wavelengths was 0) or all of the red wavelengths have fully decayed (the light has traveled far enough to fully decay).

For the examples provided here, data was gathered at an underwater ocean environment location on the West side of Oahu in the Hawaiian Islands. The location featured a gently sloping ocean floor at depths of 5-12 meters, with visibility exceeding 20 meters to promote absorption of a desired wavelength rather than scattering. A GOPRO HERO 4 was selected as a camera. The camera mounted on a tripod and taken to depths of 5-10 meters of water and placed at various distances from natural and manmade objects. Video footage was taken at each location with two filters (FLIP4 "Dive" and "Deep") and also without a filter. Data was collected during five dives over a two-day period at various times of day and night. Diver one set up the tripod and operated the filters during all data collection. Diver two measured the distance to a known object for reference for each dataset. Video footage was processed using PINNACLE 19 to obtain still images. Images were cropped to provide each pair of filtered and unfiltered images with the same field of view. A filtered image and the corresponding unfiltered image were processed as a pair using MATLAB R2015b Image Processing toolbox and user generated code.

Water temperature, salinity, and density were measured using an RBR CONCERTO. Averages for each dive were calculated and compiled as indicated in TABLE 1. A temperature of 27.55° C. was used as the average temperature, 34.60 PSU, or g/kg, was used as the average salinity, and 22.27 kg/m$^3$ was used as the average density. These average values produced a temperature and salinity corrected absorption coefficient of 0.00689 m$^{-1}$. For light in the red bandwidth, this salinity corrected absorption coefficient value was utilized for an image distance expression $d_r$=−0.14517 ln ($R_u/R_f$) and produced the relative distance $d_r$ given in mm.

Image pairs were captured as described above with RGB matrices produced for each. For each (x,y) pixel, an $R_u$ value from the unfiltered image was divided by an $R_f$ value from the filtered image. This produced a new matrix of relative distances for each (x,y) pixel value. This matrix was represented as a three-dimensional wire-mesh with colored peaks indicating distances. In certain embodiments and for some pixels, the boundary condition mentioned above created extraneous peaks skewing the results. As a result, code was added to search for pixels whose value exceed a threshold, and those pixels were set to a nominal value to avoid skewing the results.

The theoretical maximum distance traveled by red wavelengths of light in clear water is generally about 10 m. The unfiltered image of FIG. 3 as well as a filtered image was taken at a depth of 8.3 m and approximately 2.0 m from the subject to the camera, so the light has traveled a total of 10.3 meters through the water. This image pair is, therefore, near the theoretical maximum distance for red light. The unfiltered image provided a matrix of light that has lost intensity and experienced a color shift as the light has traveled from the surface to the subject and from the subject to the camera. The image appeared washed out, mostly showing greens and blues, as is common for unfiltered underwater photography. In contrast, the filtered image represents a close approximation of the original colors of the subject, fleeting the color balance restored by using the filter After fully processing the images, the results were displayed as the 3D wire-mesh of FIG. 4. For each (x,y) pixel in the image, an image distance $d_r$ value was determined to describe a relative distance. At FIG. 4, the coral is visible with peaks indicating where the coral sticks out farther or is closer to the camera.

Figure 6:
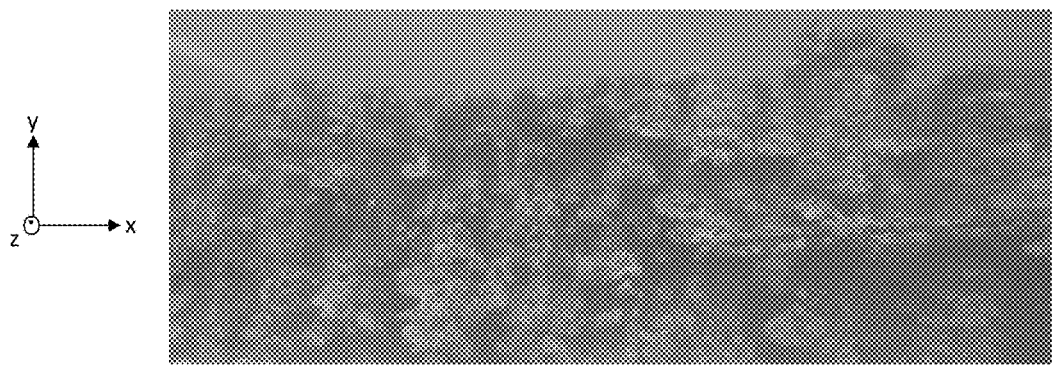
FIG. 6 illustrates an image of a second object.
Figure 7:
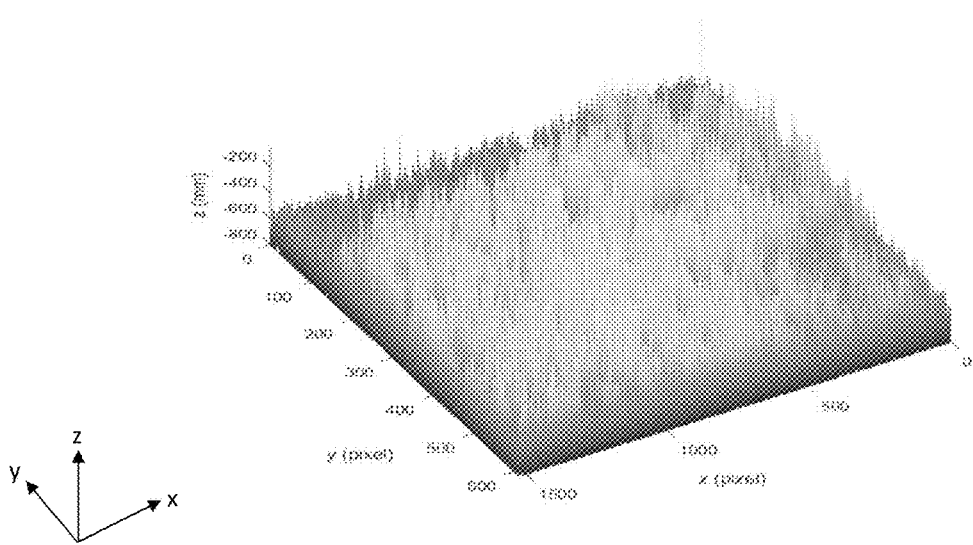
FIG. 7 illustrates a 3D point cloud of the second object.

The same subject photographed at a range of 5.0 m and a depth of 8.3 m is shown at FIG. 6. Comparison of the unfiltered and filtered images generated the 3D wire-mesh illustrated at FIG. 7. Adding these distances 5.0 m and 8.3 m together gives a total distance of 13.3, which is 33% larger than the theoretical maximum distance of 10 m that the red wavelengths generally can travel. The expected result is less resolution because some of the filtered pixel values have reached zero. Comparing the features of FIG. 4 and FIG. 7, images of the same coral provide significantly less resolution. The same features are still visible but less prominent. Some red wavelengths did still reach the camera, so 13.3 m is not an absolute maximum for the red wavelengths to travel, but it does indicate that using red wavelengths is less accurate at this distance.

Figure 8:
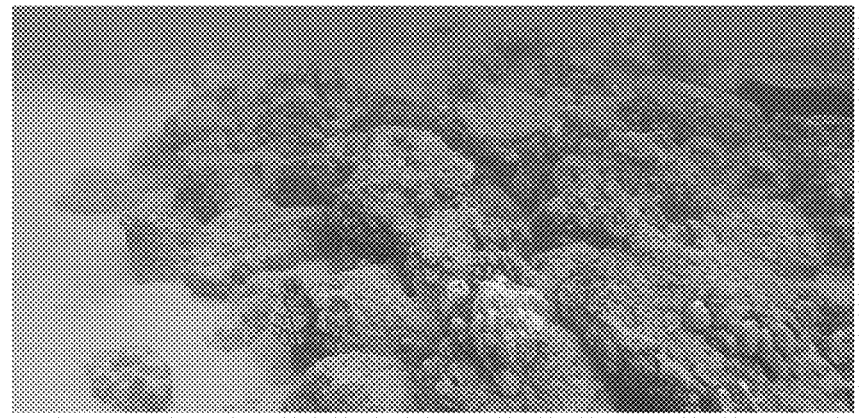
FIG. 8 illustrates an image of a third object.
Figure 9:
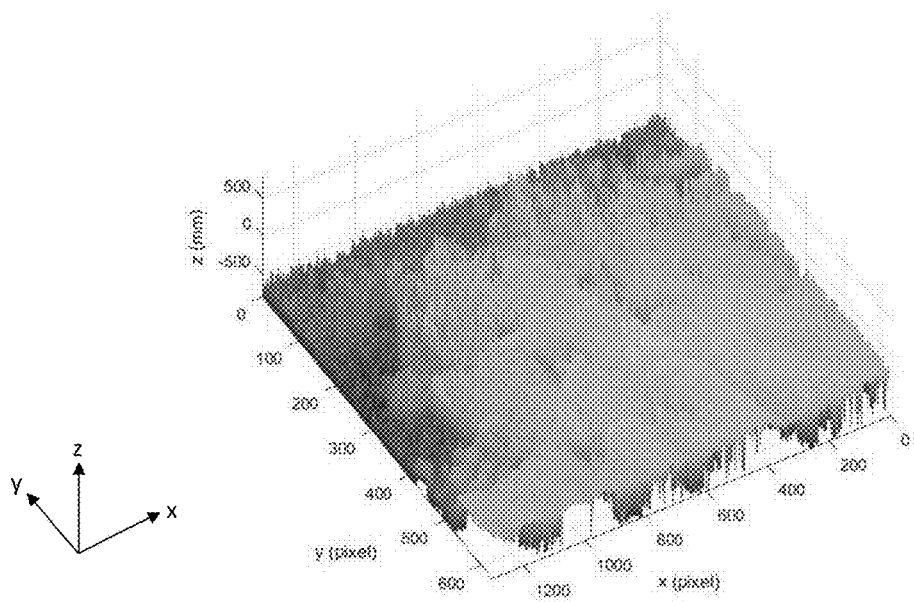
FIG. 9 illustrates a 3D point cloud of the third object.

A separate subject taken at a shallower depth (5.0 m) and range of 2.0 m illustrated at FIG. 8. Processing the unfiltered and filtered images and using the red filter provided the 3D wire-mesh illustrated at FIG. 9.

The results demonstrate the effectiveness of the method and apparatus for robot vision, and in particular its suitability for underwater environments. The technique is vision-based and may be performed with a processor, camera, a filter, and sufficient natural light. By comparing two raw images, one filtered and one unfiltered, the method and apparatus generates a detailed three-dimensional image showing the relative distance between objects in a scene. In particular embodiments, this is done by separating the color in each pixel into its respective red, green, and blue values. The red and blue values shift toward the green corner in the RGB color space as the light travels through a medium such as water. Analyzing the amount these values shift approximates relative distances between objects in the frame. Capturing and processing these images provides a determination of the relative ranges.

Thus, described here is an apparatus and method allowing a robot vision system to generate a 3D point cloud of a surrounding environment through comparison of unfiltered and filtered images of the surrounding environment. A filtered image is captured using a camera filter which tends to pass certain wavelength bandwidths while mitigating the passage of other bandwidths. A processor receives the unfiltered and filtered images, pixel matches the unfiltered and filtered images, and determines an image distance for each pixel based on comparing the color coordinates determined for that pixel in the unfiltered and filtered image. The image distances determined provides a relative distance from the digital camera to an object or object portion captured by each pixel, and the relative magnitude of all image distances determined for all pixels in the unfiltered and filtered images allows generation of a 3D point cloud representing the object captured in the unfiltered and filtered images.

Accordingly, this description provides exemplary embodiments of the present invention. The scope of the present invention is not limited by these exemplary embodiments. Numerous variations, whether explicitly provided for by the specification or implied by the specification or not, may be implemented by one of skill in the art in view of this disclosure.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

TABLE 1

Averaged Data from RBR Probe

| Dive # | Temp °C. | Salinity PSU | Density kg/m$^3$ | $C_s$ g/l |
|---|---|---|---|---|
| 1 | 27.41805 | 33.84613 | 21.73631 | 0.73569 |
| 2 | 27.72177 | 34.70507 | 22.28743 | 0.773487 |
| 3 | 27.5493 | 34.7634 | 22.38712 | 0.778252 |
| 4 | 27.42537 | 34.75553 | 22.42119 | 0.77926 |
| Average | 27.54915 | 34.60401 | 22.26674 | 0.770519 |

What is claimed is:

1. A robot vision apparatus comprising:
   an imaging apparatus comprising:
      one or more digital cameras comprising a specific camera and the specific camera having a field-of-view, where each of the one or more digital cameras is programmed to capture an image and generate a pixmap of the image, where the pixmap comprises a plurality of pixels, where each pixel comprises a pixel value referenced to a color table, where the color table represents a plurality of colors where each color is referenced to at least a first primary color by a first color space coordinate and a second primary color by a second color space coordinate, where the first primary color represents a first wavelength bandwidth of light wavelengths and the second primary color represents a second wavelength bandwidth of light wavelengths;
      a camera filter having a Full Width at Half Maximum (FWHM) bandwidth where a specific light wavelength is within the first wavelength bandwidth of light wavelengths and within the FWHM bandwidth of the camera filter; and
      a filter mechanism mechanically configured to position the camera filter in at least a filtering position, where the filtering position is within the field of view of the specific camera; and
   a processor in data communication with the imaging apparatus and the processor programmed to generate a point cloud in a coordinate system by performing steps comprising:
      generating an unfiltered pixmap comprising unfiltered pixels and a filtered pixmap comprising filtered pixels by performing steps comprising:
         directing the imaging apparatus to capture an unfiltered image and generate the unfiltered pixmap using an individual camera comprising the one or more cameras, where the individual camera has an individual field of view and where the filter is not within the individual field of view of the individual camera, thereby generating the unfiltered pixmap comprising the unfiltered pixels;
         directing the imaging apparatus to capture a filtered image and generate the filtered pixmap using the specific camera and with the camera filter in the filtering position, thereby generating the filtered pixmap comprising the filtered pixels; and
retrieving the unfiltered pixmap comprising the unfiltered pixels and the filtered pixmap comprising the filtered pixels from the imaging apparatus;
pixel matching the unfiltered pixmap and the filtered pixmap and generating a plurality of match pairs, where each match pair associates a specific unfiltered pixel comprising the unfiltered pixmap with a specific filtered pixel comprising the filtered pixmap, and where the each match pair is assigned an (x,y) pair coordinate based on a location of the specific unfiltered pixel in the unfiltered pixmap and a location of the specific filtered pixel in the filtered pixmap, thereby generating the plurality of match pairs; and
generating the point cloud in the coordinate system using the plurality of match pairs, where the coordinate system has at least a first dimension, a second dimension, and a third dimension, by, for each match pair comprising the plurality of match pairs, performing steps comprising:
extracting an unfiltered first color space coordinate from the unfiltered pixel of the each matched pair, where the unfiltered first color space coordinate is referenced to the first primary color;
extracting a filtered first color space coordinate from the filtered pixel of the each matched pair, where the filtered first color space coordinate is referenced to the first primary color;
determining an image distance for the each match pair using a difference between a logarithm of a first term and a logarithm of a second term, where the first term comprises the unfiltered first color space coordinate of the each match pair and the second term comprises the filtered first color space coordinate of the each match pair; and
generating a data point for the each match pair in the coordinate system by using the (x,y) pair coordinate assigned to the each match pair to define a coordinate in the first dimension and a coordinate in the second dimension and using the image distance for the each match pair to define a coordinate in the third dimension, thereby generating the point cloud in the coordinate system.

2. The robot vision apparatus of claim 1 where the processor is programmed to determine the image distance for the each match pair using the difference between the logarithm of the first term and the logarithm of the second term, and where the difference between the logarithm of the first term and the logarithm of the second term divided by a value $\Delta R$ is greater than 0.75 and less than 1.25, where the value $\Delta R$ is equal to a scaling factor multiplied by a difference between a logarithm of the unfiltered first color space coordinate for the each match pair and a logarithm of the filtered first color space coordinate for the each match pair, where the scaling factor is a constant value for all match pairs comprising the plurality of match pairs.

3. The robot vision apparatus of claim 1 where the first wavelength bandwidth of the first primary color comprises a first center wavelength and the second wavelength bandwidth of the second primary color comprises a second center wavelength, and the first center wavelength is greater than the second center wavelength.

4. The robot vision apparatus of claim 3 where the color table referenced by the each pixel comprising the pixmap defines a point in an additive color space, where the additive color space has at least a first dimension corresponding to the first color space coordinate and a second dimension corresponding to the second color space coordinate.

5. The robot vision apparatus of claim 4 where the each color represented by the color table is further referenced to at least a third primary color by a third color space coordinate, where the third primary color represents a third wavelength bandwidth of light, and where the additive color space has at least a third dimension corresponding to the third color space coordinate.

6. The robot vision apparatus of claim 5 where the first wavelength bandwidth of light, the second wavelength bandwidth of light, and the third wavelength bandwidth of light each comprise one or more wavelengths in the visible spectrum.

7. The robot vision apparatus of claim 4 further comprising a temperature detector and a salinity detector, and where the processor is further programmed to perform steps comprising:
retrieving a temperature measurement from the temperature detector;
retrieving a salinity measurement from the salinity detector;
retrieving an uncorrected absorption coefficient value for the specific wavelength of light within the first wavelength bandwidth of light wavelengths and within the FWHM bandwidth of the camera filter, and correcting the uncorrected absorption coefficient value using the temperature measurement and the salinity measurement to generate a corrected absorption coefficient value; and
determining the image distance for the each match pair using the difference between the logarithm of the first term and the logarithm of the second term and using the corrected absorption coefficient value.

8. The robot vision apparatus of claim 7 further comprising:
a platform attached to the imaging apparatus and the processor; and
a volume of water surrounding the platform, the imaging apparatus, and the processor.

9. The robot vision apparatus of claim 7 where the one or more digital cameras comprise a first digital camera and a second digital camera and where the camera filter is within a field of view of the second digital camera when the filter mechanism positions the camera filter in the filtering position, and where the processor is further programmed to perform steps comprising:
directing the imaging apparatus to capture the unfiltered image and generate the unfiltered pixmap using the first digital camera; and
directing the imaging apparatus to capture the filtered image and generate the filtered pixmap using the second digital camera.

10. The robot vision apparatus of claim 7 where the one or more digital cameras comprises a single digital camera and where the camera filter is within a field of view of the single digital camera when the filter mechanism positions the camera filter in the filtering position, and where the processor is further programmed to perform steps comprising:
directing the imaging apparatus to capture the unfiltered image and generate the unfiltered pixmap using the single digital camera when the camera filter is not in the filtering position; and directing the imaging apparatus to capture the filtered image and generate the filtered pixmap using the single digital camera when the camera filter is in the filtering position.

11. A method of generating a point cloud in a coordinate system where the point cloud represents an object comprising:

obtaining one or more digital cameras where each of the one or more digital cameras is programmed to capture an image and generate a pixmap of the image, where the pixmap comprises a plurality of pixels, where each pixel comprises a pixel value referenced to a color table, where the color table represents a plurality of colors where each color is referenced to at least a first primary color by a first color space coordinate and a second primary color by a second color space coordinate, where the first primary color represents a first wavelength bandwidth of light wavelengths and the second primary color represents a second wavelength bandwidth of light wavelengths;

capturing an unfiltered image of the object and generating an unfiltered pixmap comprising unfiltered pixels using an individual camera comprising the one or more digital cameras;

capturing a filtered image of the object and generating a filtered pixmap comprising filtered pixels using a specific digital camera comprising the one or more cameras and a camera filter, where the specific digital camera has a field of view, and where the camera filter has a Full Width at Half Maximum (FWHM) bandwidth where a specific light wavelength is within the first wavelength bandwidth of light wavelengths and within the FWHM bandwidth of the camera filter, and where the camera filter is within the field of view of the specific digital camera and between the specific digital camera and the object;

generating the point cloud in the coordinate system comprising at least a first dimension, a second dimension, and a third dimension by communicating the unfiltered pixmap and the filtered pixmap from the one or more digital cameras to a processor, where the processor is programmed to perform steps comprising:

pixel matching the unfiltered pixmap and the filtered pixmap and generating a plurality of match pairs, where each match pair associates a specific unfiltered pixel comprising the unfiltered pixmap with a specific filtered pixel comprising the filtered pixmap, and where the each match pair is assigned an (x,y) pair coordinate based on a location of the specific unfiltered pixel in the unfiltered pixmap and a location of the specific filtered pixel in the filtered pixmap, thereby generating the plurality of match pairs;

generating the point cloud in the coordinate system by, for each match pair comprising the plurality of match pairs, performing steps comprising:

extracting an unfiltered first color space coordinate from the unfiltered pixel of the each matched pair, where the unfiltered first color space coordinate is referenced to the first primary color;

extracting a filtered first color space coordinate from the filtered pixel of the each matched pair, where the filtered first color space coordinate is referenced to the first primary color;

determining an image distance for the each match pair using a difference between a logarithm of a first term and a logarithm of a second term, where the first term comprises the unfiltered first color space coordinate of the each match pair and the second term comprises the filtered first color space coordinate of the each match pair; and generating a data point for the each match pair in the coordinate system by using the (x,y) pair coordinate assigned to the each match pair to define a coordinate in the first dimension and a coordinate in the second dimension and using the image distance for the each match pair to define a coordinate in the third dimension, thereby generating the point cloud in the coordinate system where the point cloud represents the object.

12. The method of claim 11 where the processor is programmed to determine the image distance for the each match pair using the difference between the logarithm of the first term and the logarithm of the second term, and where the difference between the logarithm of the first term and the logarithm of the second term divided by a value $\Delta R$ is greater than 0.75 and less than 1.25, where the value $\Delta R$ is equal to a scaling factor multiplied by a difference between a logarithm of the unfiltered first color space coordinate for the each match pair and a logarithm of the filtered first color space coordinate for the each match pair, where the scaling factor is a constant value for all match pairs comprising the plurality of match pairs.

13. The method of claim 11 where the processor is further programmed to retrieve an uncorrected absorption coefficient value for the specific wavelength of light and correct the uncorrected absorption coefficient value using a temperature measurement and a salinity measurement and thereby obtain the absorption coefficient value for the specific wavelength of light, and further comprising:

surrounding the object and the one or more digital cameras by a volume of water;
determining a temperature of the volume of water;
determining a salinity of the volume of water; and
providing the temperature of the volume of water and the salinity of the volume of water to the processor.

14. The method of claim 13 where the first wavelength bandwidth of the first primary color comprises a first center wavelength and the second wavelength bandwidth of the second primary color comprises a second center wavelength, and the first center wavelength is greater than the second center wavelength.

15. The method of claim 12 where the color table referenced by the each pixel comprising the pixmap defines a point in an additive color space, where the additive color space has at least a first dimension corresponding to the first color space coordinate and a second dimension corresponding to the second color space coordinate.

16. The method of claim 15 where the each color represented by the color table is further referenced to at least a third primary color by a third color space coordinate, where the third primary color represents a third wavelength bandwidth of light, and where the additive color space has at least a third dimension corresponding to the third color space coordinate.

17. The method of claim 16 where the first wavelength bandwidth of light, the second wavelength bandwidth of light, and the third wavelength bandwidth of light each comprise one or more wavelengths in the visible spectrum.

18. A robot vision apparatus comprising:
an imaging apparatus comprising:
one or more digital cameras comprising a specific camera and the specific camera having a field-of-view, where each of the one or more digital cameras is programmed to capture an image and generate a pixmap of the image, where the pixmap comprises a plurality of pixels, where each pixel comprises a pixel value referenced to a color table, where the color table represents a plurality of colors where each color is referenced to at least a first primary color by a first color space coordinate and a second primary color by a second color space coordinate, and where the first primary color represents a first wavelength bandwidth of light wavelengths and the second primary color represents a second wavelength bandwidth of light wavelengths, and where the first wavelength bandwidth comprises a first center wavelength and the second wavelength bandwidth comprises a second center wavelength, and the first center wavelength is greater than the second center wavelength;

a camera filter having a Full Width at Half Maximum (FWHM) bandwidth where a specific light wavelength is within the first wavelength bandwidth of light wavelengths and within the FWHM bandwidth of the camera filter;

a filter mechanism mechanically configured to position the camera filter in at least a filtering position, where the filtering position is within the field of view of the specific camera;

a processor in data communication with the imaging apparatus and the processor programmed to generate a point cloud in a coordinate system by performing steps comprising:

generating an unfiltered pixmap comprising unfiltered pixels and a filtered pixmap comprising filtered pixels by performing steps comprising:

directing the imaging apparatus to capture an unfiltered image and generate the unfiltered pixmap using an individual camera comprising the one or more cameras, where the individual camera has an individual field of view and where the filter is not within the individual field of view of the individual camera, thereby generating the unfiltered pixmap comprising the unfiltered pixels;

directing the imaging apparatus to capture a filtered image and generate the filtered pixmap using the specific camera and with the camera filter in the filtering position, thereby generating the filtered pixmap comprising the filtered pixels; and retrieving the unfiltered pixmap comprising the unfiltered pixels and the filtered pixmap comprising the filtered pixels from the imaging apparatus;

pixel matching the unfiltered pixmap and the filtered pixmap and generating a plurality of match pairs, where each match pair associates a specific unfiltered pixel comprising the unfiltered pixmap with a specific filtered pixel comprising the filtered pixmap, and where the each match pair is assigned an (x,y) pair coordinate based on a location of the specific unfiltered pixel in the unfiltered pixmap and a location of the specific filtered pixel in the filtered pixmap, thereby generating the plurality of match pairs;

generating the point cloud in the coordinate system using the plurality of match pairs, where the coordinate system has at least a first dimension, a second dimension, and a third dimension, by, for each match pair comprising the plurality of match pairs, performing steps comprising:

extracting an unfiltered first color space coordinate from the unfiltered pixel of the each matched pair, where the unfiltered first color space coordinate is referenced to the first primary color;

extracting a filtered first color space coordinate from the filtered pixel of the each matched pair, where the filtered first color space coordinate is referenced to the first primary color;

determining an image distance for the each match pair using a difference between a logarithm of a first term and a logarithm of a second term, where the first term comprises the unfiltered first color space coordinate of the each match pair and the second term comprises the filtered first color space coordinate of the each match pair, and where the difference between the logarithm of the first term and the logarithm of the second term divided by a value $\Delta R$ is greater than 0.75 and less than 1.25, where the value $\Delta R$ is equal to a scaling factor multiplied by a difference between a logarithm of the unfiltered first color space coordinate for the each match pair and a logarithm of the filtered first color space coordinate for the each match pair, where the scaling factor is a constant value for all match pairs comprising the plurality of match pairs; and generating a data point for the each match pair in the coordinate system by using the (x,y) pair coordinate assigned to the each match pair to define a coordinate in the first dimension and a coordinate in the second dimension and using the image distance for the each match pair to define a coordinate in the third dimension, thereby generating the point cloud in the coordinate system.

19. The robot vision apparatus of claim 18 where the each color represented by the color table is further referenced to at least a third primary color by a third color space coordinate, and where the color table referenced by the each pixel comprising the pixmap defines a point in an additive color space, where the additive color space has at least a first dimension corresponding to the first color space coordinate, a second dimension corresponding to the second color space coordinate, and a third dimension corresponding to the third color space coordinate.

20. The robot vision apparatus of claim 19 further comprising a temperature detector and a salinity detector, and where the processor is further programmed to perform steps comprising:

retrieving a temperature measurement from the temperature detector;

retrieving a salinity measurement from the salinity detector;

retrieving an uncorrected absorption coefficient value for the specific wavelength of light within the first wavelength bandwidth of light wavelengths and within the FWHM bandwidth of the camera filter, and correcting the uncorrected absorption coefficient value using the temperature measurement and the salinity measurement to generate a corrected absorption coefficient value; and determining the image distance for the each match pair using the difference between the logarithm of the first term and the logarithm of the second term and using the corrected absorption coefficient value.

\* \* \* \* \*